United States Patent [19]
Machek et al.

[11] Patent Number: 5,800,495
[45] Date of Patent: Sep. 1, 1998

[54] ENDOCARDIAL LEAD ASSEMBLY

[75] Inventors: James E. Machek, Lake Jackson, Tex.; Yves Verboven, Kessel-lo, Belgium; Paul R. Spehr, Lake Jackson; Stephen L. Goldman, Missouri City, both of Tex.

[73] Assignee: Sulzer Intermedics Inc., Angleton, Tex.

[21] Appl. No.: 828,793

[22] Filed: Mar. 27, 1997

[51] Int. Cl.⁶ .................................................. A61N 1/05
[52] U.S. Cl. ............................................... 607/116
[58] Field of Search .................... 604/85, 102, 264; 600/16–18, 704–705; 607/116, 119, 120, 122

[56]           References Cited
          U.S. PATENT DOCUMENTS 3,411,507  11/1968  Wingrove ................................. 604/21
3,995,617  12/1976  Watkins et al. ........................... 600/16
5,486,160   1/1996  Rossi et al. .............................. 604/21

*Primary Examiner*—William E. Kamm
*Attorney, Agent, or Firm*—John R. Merkling; Fletcher, Yoder & Associates

[57]            ABSTRACT

Various endocardial lead assemblies are disclosed that may be particularly useful for placement within the coronary sinus. One lead assembly includes an open-ended electrode that may be implanted in a patient by passing it along a previously implanted stylet. Another disclosed embodiment combines an open-ended electrode with one or more flow passages that improve blood flow through the body vessel in the area of the implanted electrode. Yet another disclosed embodiment uses an electrode that has flow passages but no opening. This electrode provides improved blood flow in the area of the electrode but may be implanted using conventional methods.

33 Claims, 6 Drawing Sheets

ENDOCARDIAL LEAD ASSEMBLY

BACKGROUND OF THE INVENTION

1. Field of the Invention

This present invention relates generally to cardiac stimulation and, more particularly, to an implantable endocardial lead assembly.

2. Description of the Related Art

For a variety of reasons, a person's heart may not function properly and, thus, endanger the person's well-being. Medical devices have been developed to facilitate heart function. For instance, if a person's heart does not beat properly, a cardiac stimulator may be used to provide relief. A cardiac stimulator, such as a pacemaker or a cardioverter/defibrillator, is a medical device that delivers electrical stimulation to a patient's heart. A cardiac stimulator generally includes a pulse generator for creating electrical stimulation pulses and at least one conductive lead having an electrode at one end for delivering these electrical stimulation pulses to the designated portion of the heart.

There are generally two types of implantable leads used with cardiac stimulators. One type requires surgical incision of the patient's chest wall to expose the myocardial tissue to which the electrode is attached. The other type involves transvenous insertion where the lead is inserted endocardially through a body vessel, such as a vein, directly into the heart. The distal end of the electrode is routed through the heart and disposed near the myocardial tissue to be paced.

Existing leads have a lumen and terminate in a closed tip at the lead's distal end. Just prior to transvenous insertion, a flexible stylet is disposed in the lumen so that the distal end of the stylet abuts the interior surface of the closed tip of the lead. The lead and the stylet are then inserted transvenously as a unit. The movement and positioning of the lead is accomplished by manipulating the proximal end of the stylet. After the distal end of the lead has been successfully positioned, the stylet is removed and the proximal end of the lead is connected to a cardiac stimulator.

Transvenous pacing of the left atrium and ventricle via the coronary sinus has become a common procedure during the past twenty-five years for both diagnosis and therapy of cardiac arrhythmias. The coronary sinus has five major venous tributaries that can be entered by pacing leads. The most common placement involves lodging the lead electrode in the great cardiac vein. However, many patients require a more esoteric placement of the lead, such as, for example, in the anterior interventricular vein.

There are certain disadvantages associated with a lead having a closed end, particularly when attempting to place the lead in the coronary sinus or one of its tributaries. For example, the distal end of the lead may present a risk of venous occlusion. A lead having a closed end may restrict blood flow, particularly in a tributary having an unusually small diameter. Furthermore, the restricted blood flow in the vicinity of the distal end of the lead may lead to embolism, which in turn may further restrict blood flow.

Aside from the potential for venous occlusion, existing leads are implanted by the simultaneous manipulation of the lead and the stylet disposed within the lead. Whereas commonly used stylets have diameters that are orders of magnitude smaller than the coronary sinus and its tributaries, existing leads may have diameters that begin to approach the diameters of the coronary sinus or its tributaries. The shear bulk of the lead in relation to the coronary sinus and its tributaries may make the implantation procedure difficult and time consuming. This situation may be exacerbated by the presence of plaque or other obstructions in the coronary sinus or its tributaries or by the patient who presents an unusually small coronary sinus or coronary sinus tributaries.

The present invention is directed to overcoming or reducing the effects of one or more of the foregoing disadvantages.

SUMMARY OF THE INVENTION

In accordance with one aspect of the present invention, there is provided a lead assembly for implantation in a patient. The lead assembly includes a lead adapted to transmit electrical impulses. The lead has a proximal end and a distal end. The lead also has a lumen that extends from the proximal end to the distal end. An electrode is coupled to the distal end of the lead. The electrode has an outer surface. The electrode also has an opening that extends therethrough and defines an inner surface. The opening is operatively positioned relative to the lumen. The lumen and the opening are sized to accept a stylet or guide wire.

In accordance with another aspect of the present invention, there is provided a lead assembly for implantation in a patient. The lead assembly includes a lead adapted to transmit electrical impulses. The lead has a proximal end and a distal end. An electrode is coupled to the distal end. The distal end has a flow passage formed therein.

In accordance with a further aspect of the present invention, there is provided a lead assembly for implantation in a patient. The lead assembly includes a lead adapted to transmit electrical impulses. The lead has a proximal end and a distal end. The lead also has a lumen that extends from the proximal end to the distal end. An electrode is coupled to the distal end of the loop. The distal end has a plurality of flow passages formed therein. The electrode also has an outer surface and an opening that extends therethrough to define an inner surface. The opening is operatively positioned relative to the lumen. The lumen and the opening are sized to accept a stylet or guide wire.

In accordance with yet another aspect of the present invention, there is provided a lead assembly for implantation in a patient. The lead assembly includes a lead that has a coiled conductor adapted to transmit electrical impulses. The conductor is coated with a biocompatible electrical insulator. The lead has a proximal end and a distal end. The lead also has a lumen extending from the proximal end to the distal end. An electrode is coupled to the distal end of the lead. The distal end has a plurality of flow passages formed therein. The electrode has an outer surface and an opening that extends therethrough to define an inner surface. The opening is operatively positioned relative to the lumen. The lumen and the opening are sized to accept a stylet or guide wire.

In accordance with still another aspect of the present invention, there is provided a method for implanting a lead assembly in a patient. A stylet having a distal end and a proximal end is provided. The distal end of the stylet is routed to a desired position in a body vessel of the patient. A lead assembly is provided that includes a lead adapted to transmit electrical impulses. The lead has a proximal end and a distal end. The lead also has a lumen that extends from the proximal end to the distal end. The lead assembly further includes an electrode that is coupled to the distal end of the lead. The electrode has an outer surface. The electrode also has an opening extending therethrough and defining an inner surface. The opening is operatively positioned relative to the lumen. The lumen and the opening are sized to accept the stylet or guide wire. The proximal end of the stylet is placed into the opening in the electrode. The electrode and the lead are routed along the stylet to place the electrode in a desired position in the body vessel. The stylet is withdrawn from the lead assembly.

In accordance with a yet further aspect of the present invention, there is provided a lead for implantation in a body vessel. The lead has a fluid passageway that extends along a given length of the lead. The fluid passageway has an inlet for passing fluid from the body vessel into the passageway and an outlet for passing fluid from the passageway into the body vessel.

In accordance with a still further aspect of the present invention, there is provided a lead assembly for implantation in a body vessel. The lead assembly includes a lead that has a fluid passageway that extends along a given length of the lead. The fluid passageway has an inlet for passing fluid from the body vessel into the passageway and an outlet for passing fluid from the passageway into the body vessel. The lead further has a proximal end portion and a distal end portion. A lumen, sized to accept a stylet or guide wire, extends from the proximal end portion to the distal end portion. A conductor is disposed in the lead. The conductor extends from the proximal end portion to the distal end portion. An electrode is coupled to the conductor at the distal end portion of the lead.

In accordance with another aspect of the present invention, there is provided a lead assembly for implantation in a body vessel. The lead assembly includes a lead that has a proximal end portion and a distal end portion. A lumen, sized to accept a stylet or guide wire, extends from the proximal end portion to the distal end portion. The lumen has an inlet for passing fluid from the body vessel into the lumen and an outlet for passing fluid from the lumen into the body vessel. A conductor is disposed in the lead. The conductor extends from the proximal end portion to the distal end portion. An electrode is coupled to the conductor at the distal end portion of the lead.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
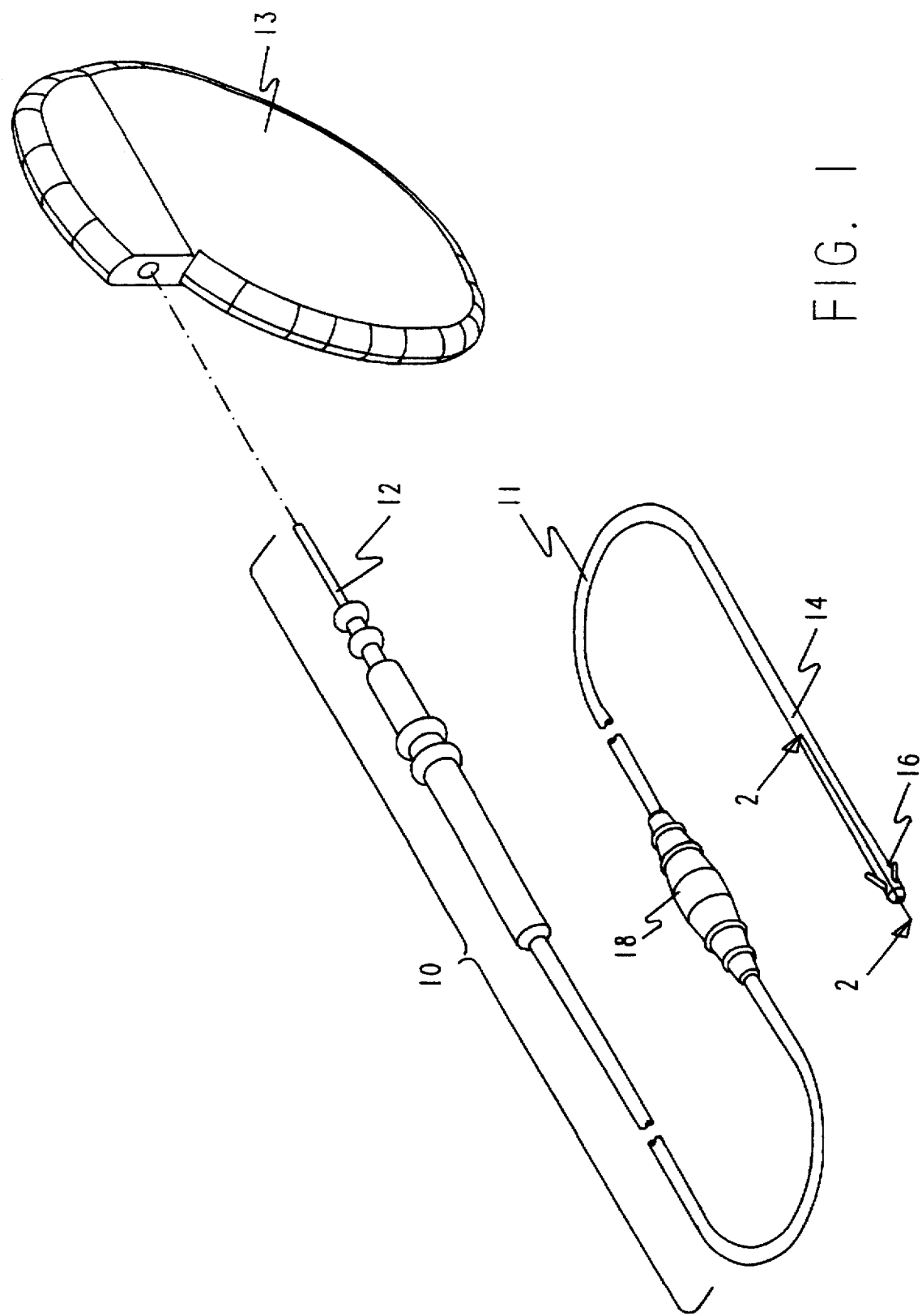
FIG. 1 illustrates an endocardial lead assembly and a cardiac stimulator.

Turning now to the drawings, FIG. 1 illustrates a pictorial representation of an endocardial lead assembly generally designated by a reference numeral 10. The lead assembly 10 is designed to be inserted endocardially through a body vessel directly into the heart. The lead assembly 10 includes a lead 11 that has a proximal end 12 that may be coupled to a cardiac stimulation device 13, such as, for example, a pacemaker or cardioverter/defibrillator. A lead such as a THINLINE™ 430-10, 430-20, or 431-11, available from the assignee, may be used. The distal end 14 of the lead 11 is attached to an electrode assembly 16. Note that the electrode assembly 16 is shown detached from the lead 11 in FIG. 1 to enable illustration of the cross-section lines 2—2. A suture sleeve 18 is slidably disposed on the lead 11. The suture sleeve 18 may be attached to the insertion vein of a patient in a conventional manner.

Figure 2:
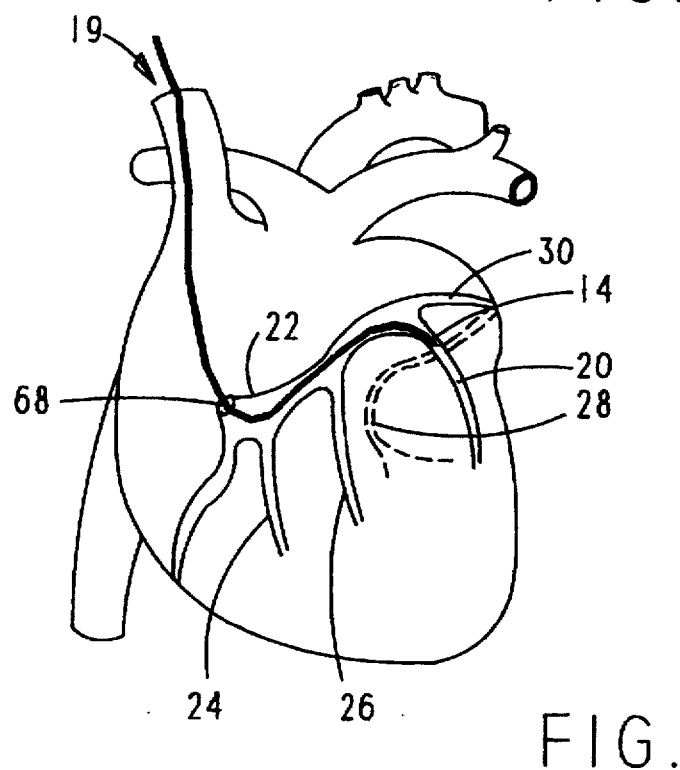
FIG. 2 illustrates an anterior view of a human heart.

The lead assembly 10 is designed to be placed within a human heart 19 as illustrated in FIG. 2. The distal end 14 of the lead 11 is shown implanted in the great cardiac vein tributary 20 of the coronary sinus 22. The lead 11 could also be placed in the coronary sinus 22 or in one of the other coronary sinus tributaries, such as the left post interventricular vein 24, the obtuse marginal vein 26, the anterior interventricular vein 28, or the great cardiac vein 30.

To facilitate placement of the lead 11 within the heart 19, as well as longevity of the lead 11 during subsequent use, the lead 11 is flexible. Also referring to FIG. 3, the lead 11 includes a flexible sheath 32 which defines a lumen 34 along the length of the lead 11. The sheath 32 is composed of a biocompatible material, such as, for example, silicone or polyurethane. A flexible coiled conductor 36 is disposed in the lumen 34. The coiled conductor 36 is coupled to the proximal end 12 of the lead assembly 10 for transmitting electrical impulses to and from the electrode assembly 16. The coiled conductor 36 may be a trifilar conductor as shown in the figures or another suitable type of conductor. The coiled conductor 36 may also be coated with a biocompatible material, such as the material described above with reference to the sheath 32, or it may be made of biocompatible conductive material.

The electrode assembly 16 includes a generally cylindrical housing 38 formed from a biocompatible conductive material, such as, for example, titanium or 300 series stainless steel. The electrode assembly 16 is advantageously coated with iridium oxide (IROX) or other suitable coating. The housing 38 has a proximal end 40 over which the sheath 32 is disposed to form a substantially sealed joint 42. A generally cylindrical crimp slug 44 is disposed inside the housing 38. The conductor 36 is wrapped around the crimp slug 30. The housing 38, the crimp slug 44, and the conductor 36 are secured together by crimping the housing 38 against the conductor 36 and the crimp slug 44. The crimp slug 44 has a longitudinal passage 46 extending therethrough to facilitate the passage of a stylet as discussed more below.

As depicted in FIG. 2, the distal end 14 of the lead 11 is disposed in the great cardiac vein 20 proximate a region 48 of reduced diameter. This narrowing of the great cardiac vein 20 is illustrative of the types of obstructions that may be encountered during implantation of the lead assembly 10 in the coronary sinus. Those knowledgeable in the field will appreciate that the constriction may be due to plaque deposits, various types of coronary artery disease, as well as peculiarities in the patient's physiology. Those knowledgeable in the field will also appreciate that a conventional closed end lead may occupy much of the available flow area for blood in the constricted region 48. This reduction in available flow area for blood may lead to embolism and less than optimal circulation.

To aid in alleviating the potential for reduced blood flow and embolism formation, the distal end 14 of the lead 11 and the electrode assembly 16 are provided with an opening 50 and one or more flow passages 52 that are longitudinally spaced from the opening 50. The direction of blood flow in the great cardiac vein 23 is indicated by the arrow 54. The opening 50 and the flow passages 52 provide a flow path for blood through the lumen 34 as shown by the flow path arrows 56. The number, configuration, and spacing of the flow passages 52 are largely a matter of design discretion.

Figure 3:
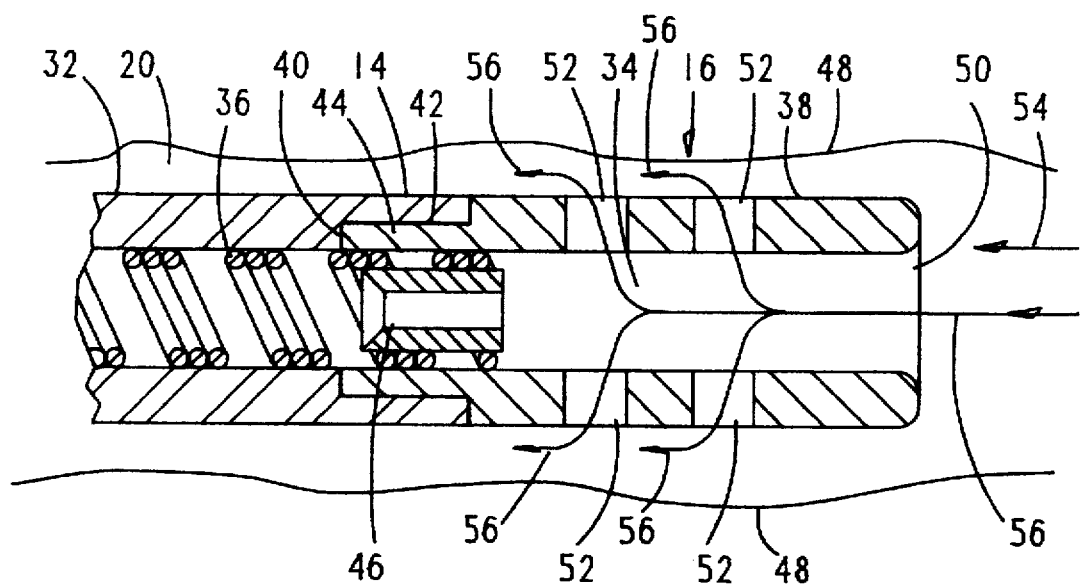
FIG. 3 illustrates a cross-sectional view of the distal end of a first embodiment of the lead assembly of FIG. 1 inserted in a vessel of the heart of FIG. 2.
Figure 4:
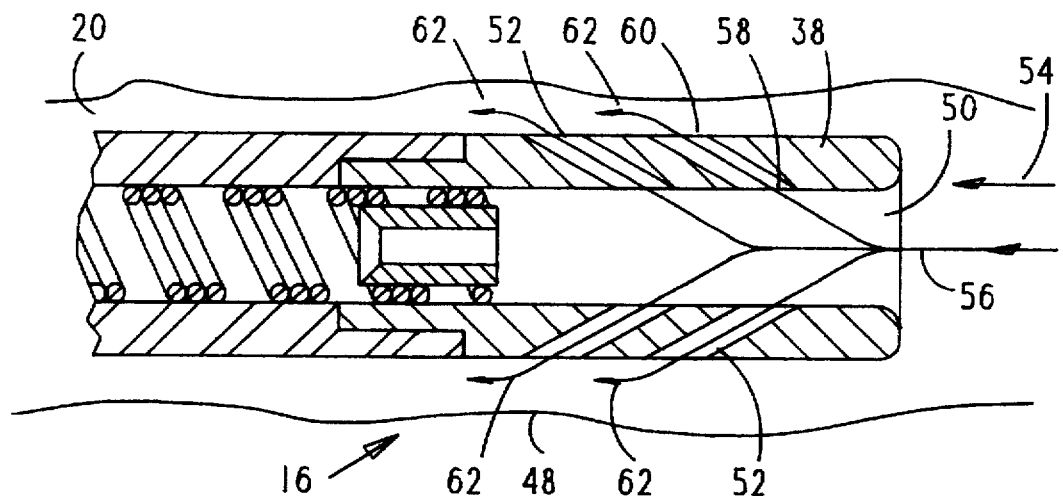
FIG. 4 illustrates a cross-sectional view of the distal end of a second embodiment of the lead assembly of FIG. 1 inserted in a vessel of the heart of FIG. 2.
Figure 5:
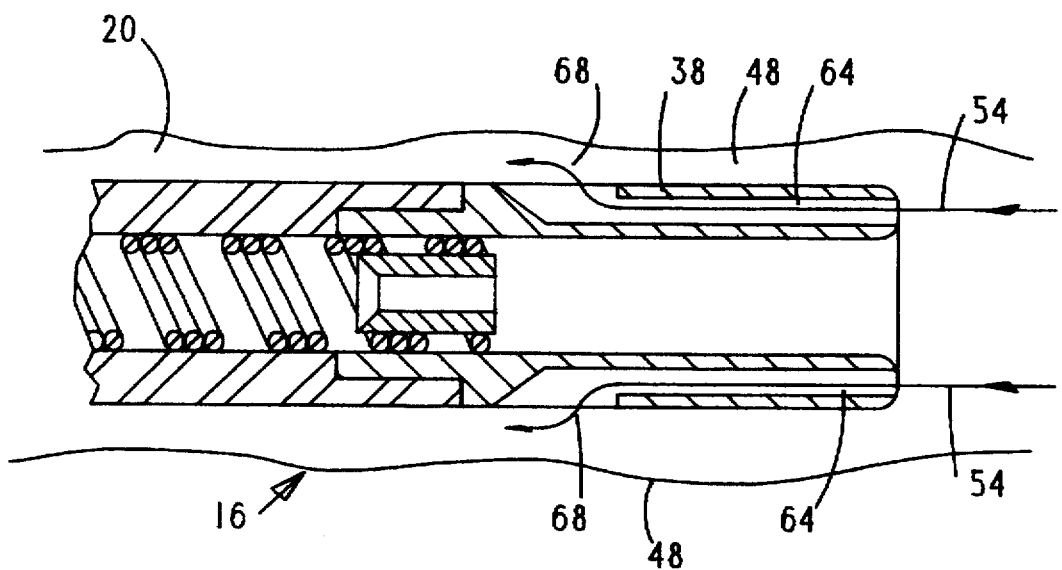
FIG. 5 illustrates a cross-sectional view of the distal end of a third embodiment of the lead assembly of FIG. 1 inserted in a vessel of the heart of FIG. 2.

In regard to the configuration of the flow passages 52, it should be noticed that the flow passages illustrated in FIG. 3 are substantially perpendicular to the longitudinal axis of the lead 11. However, different configurations of the flow passages 52 may enhance flow characteristics. For example, in an alternate embodiment shown in FIG. 4, the flow passages 52 are formed in the electrode assembly 16 so that the inlet 58 of each flow passage 52 is disposed upstream from the outlet 60 to provide a somewhat straighter flow path through the lumen 34 as indicated by the flow arrows 62. In another alternate embodiment shown in FIG. 5, blood flow is facilitated by one or more longitudinal passages 64 formed in the housing 38 of the electrode assembly 16. The outlets 66 of the longitudinal passages 64 are obliquely disposed to provide a semi-linear flow path for the blood as indicated by the flow arrows 68. As with the flow passages 62 shown in FIG. 2, the number, size, and spacing of the flow passages 52 shown in FIG. 4 and the longitudinal flow passages 64 shown in FIG. 5 are a matter of design discretion.

In the embodiments described above, the lumen 34, and thus the coiled conductor 36, are exposed to blood flow. It is possible that the blood or other bodily fluids may interfere with the functioning of the coiled conductor 36. For instance, the fluids may produce electrical interference or short circuiting. Accordingly, it may be desirable to insulate the coiled conductor 36 electrically from the blood or other body fluids to avoid this interference. The coiled conductor 36 may coated with a biocompatible insulating material, such as, for example, polyethylene tetrafluoride, polyimide, ETFE, or other suitable biocompatible insulating materials.

Because the distal end 14 of the lead assembly 10 is open instead of closed, the lead 10 may be implanted in a manner different from conventional leads. In short, a stylet may first be properly positioned within a heart. Then, the opening 50 may be slipped over the stylet so that the stylet passes into the lumen 34. The lead 11 follows the stylet until the distal end 14 of the lead assembly 10 is similarly positioned. The stylet may then be removed. Because this method of implantation may be advantageous even in areas where constriction or impaired flow may not be a problem, the electrode assembly 16 may simply incorporate the opening 50 without the flow passages 52, as illustrated in FIG. 7.

Figure 7:
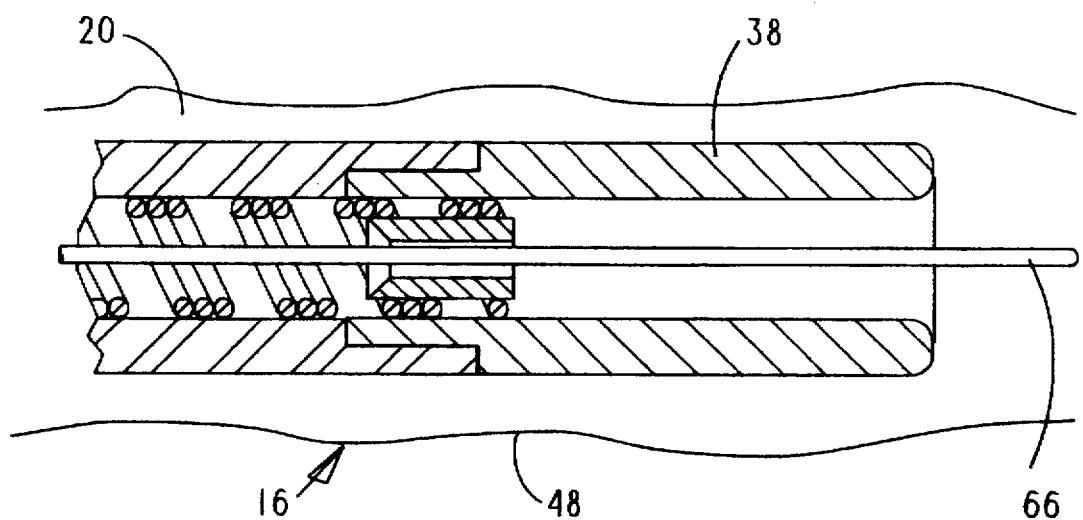
FIG. 7 illustrates a cross-sectional view of the distal end of a fourth embodiment of the lead assembly of FIG. 1 inserted in a vessel of the heart of FIG. 2 along the stylet of FIG. 6.
Figure 6:
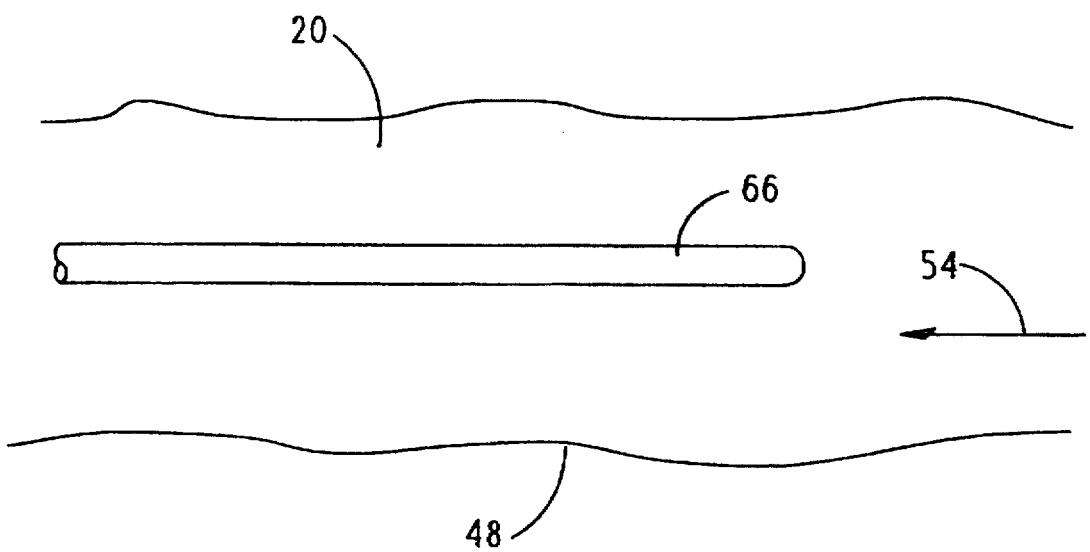
FIG. 6 illustrates a stylet inserted in a vessel of the heart of FIG. 2.

A more detailed explanation of a method for implanting the lead assembly 10 into the coronary sinus of a human heart may be understood by reference to FIGS. 2, 6, and 7. The coronary sinus 22 is commonly entered from a vein on the left side of a person's body, such as the cephalic or subclavian (not shown). Hence, the stylet 66 is inserted into the appropriate body vessel and manipulated, usually with the aid of fluoroscopy, until it reaches the heart. Following transvenous insertion of the stylet 66 into the right atrium of the heart, the stylet 66 is manipulated to avoid the tricuspid valve (not shown) and enter the coronary sinus ostium 68. Longitudinal force is then applied to the stylet 66 to advance the distal end of the stylet 66 into the desired tributary of the coronary sinus 22, in this case the great cardiac vein 20. Fluoroscopy may be used to confirm the proper positioning of the stylet 66. Lateral fluoroscopy may be helpful in confirming the typical posterior location of the stylet 66 in the coronary sinus 22 that is different from an anteriorly directed pulmonary artery position.

After the stylet 66 has been successfully positioned, the distal end 14 of the lead 11 is slipped over the proximal end (not shown) of the stylet 66. This is accomplished by inserting the proximal end of the stylet 66 into the opening 50 in the distal end 14. The distal end 14 is then advanced longitudinally with respect to the stylet 66 so that the stylet 66 slides through the passage 46 in the crimp slug 44 and into the lumen 34. The lead 11 is then advanced transvenously into the great cardiac vein 20 as shown in FIG. 7. Since the stylet 66 is already in place, the lead 11 slides easily through the body vessels using the stylet 66 as a guide. After the lead 11 has been properly positioned, the stylet 66 is withdrawn from the body leaving the lead 11 in place as shown in FIG. 2.

Figure 8:
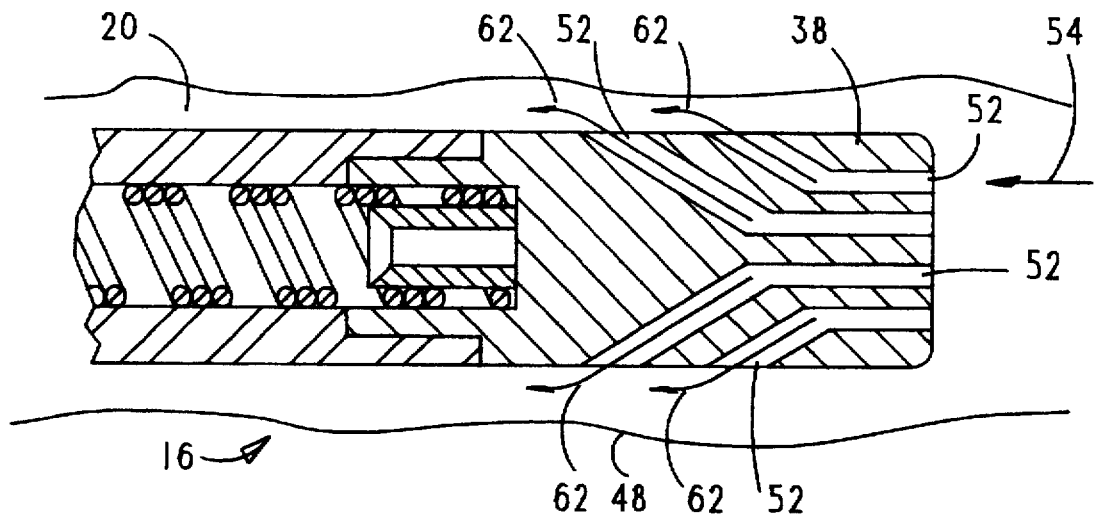
FIG. 8 illustrates a cross-sectional view of the distal end of a fifth embodiment of the lead assembly of FIG. 1 inserted in a vessel of the heart of FIG. 2.

As described above, the lead assembly 10 may be advantageous even if the electrode assembly 16 simply incorporates the opening 50 without the flow passages 52. Similarly, the lead assembly 10 may be advantageous where the electrode assembly 16 simply incorporates the flow passages 52 without the opening 50. As illustrated in FIG. 8, the housing 38 of the electrode assembly 16 incorporates a plurality of flow passages 52, but it does not include an opening 50 capable of accepting the stylet 66. Accordingly, the electrode assembly 16 effectively closes the distal end 14 of the lead 11. Thus, the embodiment of the lead assembly 10 illustrated in FIG. 8 may be advantageously used in situations where the lead assembly 10 may be implanted using conventional techniques but where enhanced blood flow may be desirable. It can be seen that the electrode assembly 16 illustrated in FIG. 8 enhances blood flow even in a constricted region 48 of a body vessel 20 because blood flowing in the direction of the arrow 54 may flow through the passageways 52 in the direction of the arrows 62.

Inflammation of the coronary sinus tissues may result from the placement of a lead in the coronary sinus 22 or any of its tributaries. Such inflammation is commonly treated by a variety of different types of anti-inflammatory drugs that are normally administered orally, but which may also be administered intravenously. However, where possible, it is desirable to deliver an anti-inflammatory agent directly to the cite of inflammation.

Figure 9:
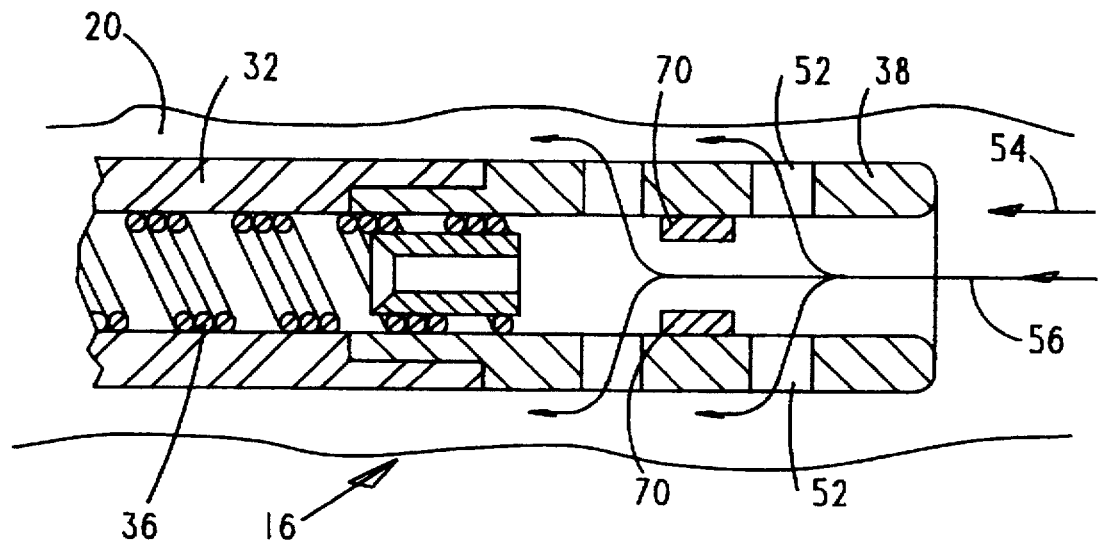
FIG. 9 illustrates a cross-sectional view of the distal end of a sixth embodiment of the lead assembly of FIG. 1 inserted in a vessel of the heart of FIG. 2.

In this regard, an alternate embodiment of the lead assembly 10 is shown in FIG. 9. In this embodiment, the electrode assembly 16 includes one or more medicated pads 70 disposed in the lumen 34, such as between the opening 50 and at least one of the flow passages 52. The medicated pads 70 form a drug elusion system by which an anti-inflammatory agent may be directly delivered to the coronary sinus via blood flowing through the lumen 34 and the flow passages 52. The medication pads 70 may be impregnated with any of a number of anti-inflammatory agents, such as steroids. The number, size, and position of the medicated pads 70 is largely a matter of design discretion, although the pads 70 should be configured to minimize potential interference with the stylet 66 during implantation.

The medicated pads 70 may be composed of a dissolvable biocompatible material, such as, for example, polyethylene glycol, dextrose, or similar biocompatible dissolvable materials. So composed, the pads 70 dissolve after they deliver the medication. Thus, the pads 70 do not remain to inhibit fluid flow through the distal end 14 of the lead 11.

Figure 10:
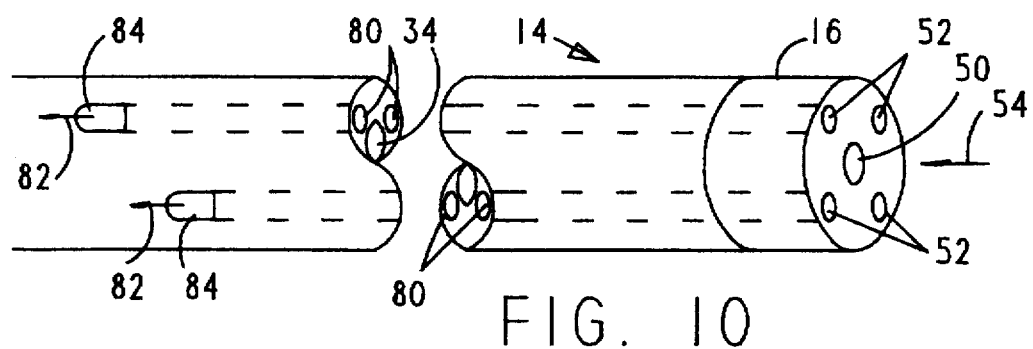
FIG. 10 illustrates a perspective view of the distal end of a seventh embodiment of the lead assembly of FIG. 1.

Although the embodiments described thus far have included passageways extending through only the electrodes, the passageways may extend through at least a portion of the lead as well. One such lead assembly 10 is illustrated in FIG. 10. To preserve the clarity of this disclosure, previously used reference numerals will be used to identify elements similar to those previously described. As illustrated in FIG. 10, an electrode assembly 16, such as a ring electrode, is coupled to the distal end 14 of the lead 11. The lead 11 includes a lumen 34 that may carry a conductor (not shown), such as the coiled conductor 36 described previously. The electrode assembly 16 may include an opening 50 that is concentric with the lumen 34 and sized to accept a stylet, so that the lead assembly 10 may be implanted using the method described with reference to FIGS. 6 and 7.

The electrode assembly 16 illustrated in FIG. 10 includes a plurality of passageways 52 that may receive fluid flowing in the direction of the arrow 54. The passageways 52 in the electrode assembly 16 are aligned with a respective plurality of passageways 80 that extend along a portion of the lead 11. Only two of the passageways 80 are illustrated in phantom lines in FIG. 10. The passageways 80 deposit fluid flowing through them in the direction of the arrows 82 into the body vessel (not shown) through outlets 84 that are positioned downstream of the electrode assembly 16. The outlets 84 may be aligned, or they may be staggered, as shown, to provide greater confidence that the fluid will flow into the body vessel in an area free from constrictions.

Figure 11:
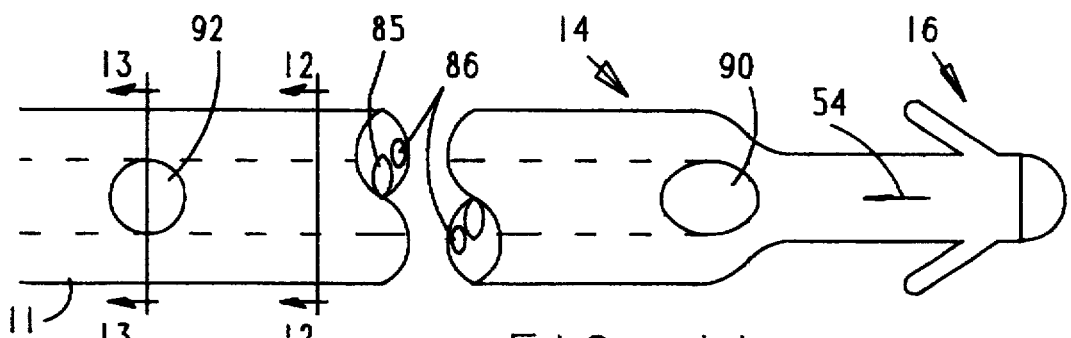
FIG. 11 illustrates a side view of the distal end of an eighth embodiment of the lead assembly of FIG. 1.

Another embodiment of the lead assembly 10 is depicted in FIG. 11. Like the embodiment of the lead assembly 10 described above with reference to FIG. 10, the embodiment of the lead assembly 10 illustrated in FIG. 11 uses the lead 11 to facilitate the flow of blood through a body vessel (not shown). However, unlike the previously described embodiment, fluid may enter the lead 11 without first passing through a passageway in the electrode assembly 16.

Figure 12:
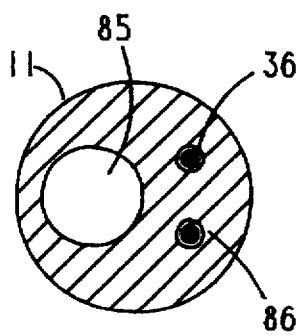
FIG. 12 illustrates a cross-sectional view of the lead of FIG. 11 taken along line 12—12.

In this embodiment, the lead 11 is a multi-lumen lead. As illustrated in FIG. 12, the lead 11 includes a main lumen 85 that is sized to accept a stylet (not shown). The conductors 36 that are coupled to the electrode assembly 16 are not disposed within the main lumen 85. Rather, the conductors 36 are disposed in secondary lumens 86 which carry the conductors 36 to the electrode assembly 16.

Figure 13:
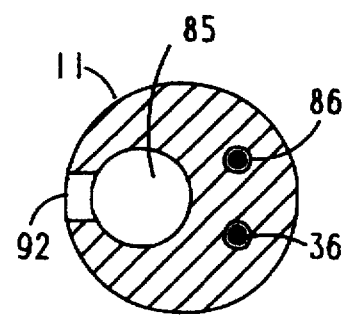
FIG. 13 illustrates a cross-sectional view of the lead of FIG. 11 taken along line 13—13.

To facilitate the flow of fluid through the body vessel, the main lumen 85 terminates in an opening 90 at the distal end 14 of the lead 11. Although the main lumen 85 extends to the proximal end of the lead 11 so that the stylet may be inserted and removed from the lead 11, the main lumen 85 includes at least one additional opening 92 located between the proximal and distal ends of the lead 11. This additional opening 92, illustrated in cross-section in FIG. 13, acts as an outlet for fluid flowing into the main lumen 85 through the opening 90 in the direction of the arrow 54. If other additional openings 92 are located between the proximal and distal ends of the lead 11, fluid may flow into one of the additional openings and out another to facilitate blood flow through any constricted portion of the body vessel.

Figure 15:
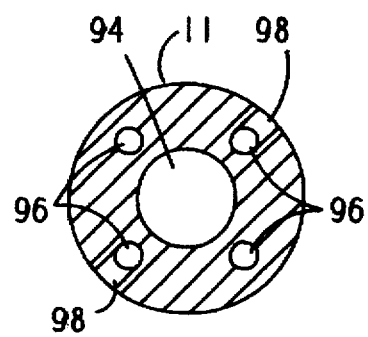
FIG. 15 illustrates a cross-sectional view of the lead of FIG. 14 taken along line 15—15.
Figure 14:
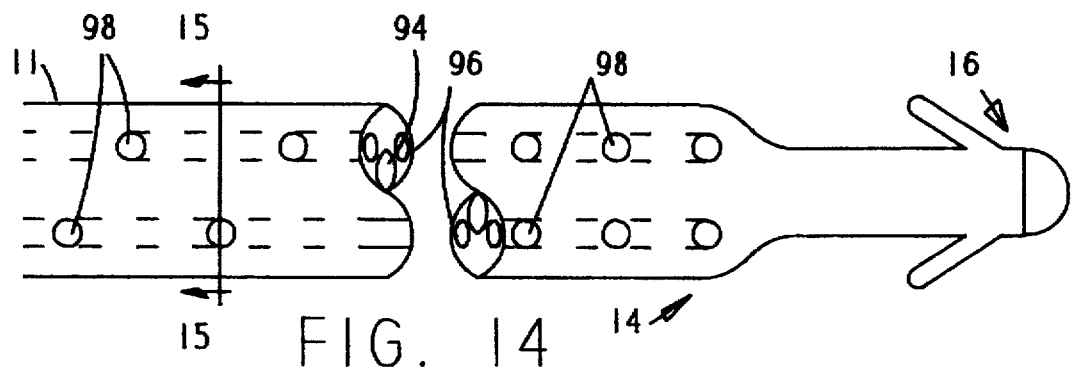
FIG. 14 illustrates a side view of the distal end of a ninth embodiment of the lead assembly of FIG. 1.

Alternatively, as illustrated in FIGS. 14 and 15, the lead 11, similar to that illustrated in FIG. 11, may include a main lumen 94 and one or more secondary lumens 96. Only two of the secondary lumens 96 are shown in phantom lines in FIG. 14. The main lumen 94 carries the conductor (not shown), such as the coiled conductor discussed previously, to the electrode assembly 16. This main lumen 94 is advantageously sized to accept a stylet so that the lead assembly 10 may be implanted by one of the methods described above, depending upon whether the electrode assembly 16 includes an opening for the stylet.

The secondary lumens 96 facilitate fluid flow, and they may extend along any given length of the lead 11 where enhanced fluid flow may be desired. The secondary lumens 96 include a plurality of openings 98 that permit fluid communication between the respective secondary lumen 96 and the body vessel into which the lead 11 is inserted. Thus, if the portion of the lead 11 along which a secondary lumen 96 extends lies within a constricted region of a body vessel, blood may flow into one or more of the openings 98 upstream of the constricted region. This blood passes into one or more of the secondary lumens 96 to bypass the constricted region and, then, flows out of the respective openings 98 located downstream of the constricted region of the body vessel. As illustrated in the two portions of the lead 11, the openings 98 may be aligned with one another or staggered.

In the embodiments discussed with reference to FIGS. 11–15, both the fluid inlet(s) and outlet(s) in the lead 11 are located downstream of the electrode assembly 16. While these embodiments may not be best suited to circumstances where a conventional electrode assembly is placed in a constricted portion of a body vessel, they are well-suited to situations where an electrode assembly is placed upstream of a constricted portion of a body vessel. Of course, in situations where the electrode assembly 16 may be placed in a constricted region of a body vessel, the electrode assembly 16 may include a housing having passageways, such as those described previously with reference to FIGS. 3–5 and 8–10.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A lead assembly for implantation in a patient, comprising:

a lead having a proximal end and a distal end, said lead having a lumen extending from said proximal end to said distal end and having an electrical conductor extending from said proximal end to said distal end; and an electrode coupled to said distal end of said lead and in electrical communication with said conductor, said electrode having an outer surface and an opening extending therethrough, said opening defining an inner surface, said lumen and said opening being sized to accept a stylet.

2. The lead assembly of claim 1, wherein said electrode further comprises:

a flow passage formed in said electrode.

3. The lead assembly of claim 2, wherein said flow passage extends in a direction perpendicular to a longitudinal axis of said electrode.

4. The lead assembly of claim 3, wherein said flow passage extends in a direction angled at less than ninety degrees relative to a longitudinal axis of said electrode.

5. The lead assembly of claim 2, wherein said flow passage extends from said inner surface to said outer surface of said electrode.

6. The lead assembly of claim 2, wherein said flow passage extends from a distal end of said electrode between said inner surface and said outer surface of said electrode to said outer surface of said electrode.

7. The lead assembly of claim 1, further comprising:

a plurality of flow passages formed in said electrode.

8. The lead assembly of claim 4, wherein said plurality of flow passages extend from said inner surface to said outer surface of said electrode.

9. The lead assembly of claim 8, wherein said plurality of flow passages extend in a direction perpendicular to a longitudinal axis of said electrode.

10. The lead assembly of claim 8, wherein said plurality of flow passages extend in a direction angled at less than ninety degrees relative to a longitudinal axis of said electrode.

11. The lead assembly of claim 4, wherein said plurality of flow passages extend from a distal end of said electrode between said inner surface and said outer surface of said electrode to said outer surface of said electrode.

12. A lead assembly for implantation in a patient, comprising:

a lead for transmitting electrical impulses, said lead having a proximal end and distal end; and an electrode coupled to said distal end, said electrode having at least one flow passage formed therein.

13. The lead assembly of claim 12, wherein said flow passage extends from an inner surface of said electrode to an outer surface of said electrode.

14. The lead assembly of claim 13, wherein said flow passage extends in a direction perpendicular to a longitudinal axis of said electrode.

15. The lead assembly of claim 13, wherein said flow passage extends in a direction angled at less than ninety degrees relative to a longitudinal axis of said electrode.

16. The lead assembly of claim 12, wherein said flow passage extends from a distal end of said electrode to a radially outer surface of said electrode.

17. The lead assembly of claim 12, wherein said electrode has a plurality of flow passages formed therein.

18. The lead assembly of claim 17, wherein said plurality of flow passages extend from an inner surface of said electrode to an outer surface of said electrode.

19. The lead assembly of claim 18, wherein said plurality of flow passages extend in a direction perpendicular to a longitudinal axis of said electrode.

20. The lead assembly of claim 18, wherein said plurality of flow passages extend in a direction angled at less than ninety degrees relative to a longitudinal axis of said electrode.

21. The lead assembly of claim 17, wherein said plurality of flow passages extend from a distal end of said electrode to a radially outer surface of said electrode.

22. A lead assembly for implantation in a patient, comprising:

a conductive lead having a proximal end and a distal end and having a lumen extending from said proximal end to said distal end; and an electrode coupled to said distal end of said lead, said electrode having a plurality of flow passages formed therein, said electrode having an outer surface and having an opening extending therethrough and defining an inner surface, said opening being operatively positioned relative to said lumen, said lumen and said opening being sized to accept a stylet.

23. The lead assembly of claim 22, wherein said plurality of flow passages extend from said inner surface to said outer surface of said electrode.

24. The lead assembly of claim 23, wherein said plurality of flow passages extend in a direction perpendicular to a longitudinal axis of said electrode.

25. The lead assembly of claim 23, wherein said plurality of flow passages extend in a direction angled at less than ninety degrees relative to a longitudinal axis of said electrode.

26. The lead assembly of claim 22, wherein said plurality of flow passages extend from a distal end of said electrode between said inner surface and said outer surface of said electrode to said outer surface of said electrode.

27. A lead for implantation in a body vessel, said lead comprising:

a lead having at least one fluid passageway extending along a given length of said lead, said fluid passageway having an inlet for passing fluid from said body vessel into said passageway and an outlet for passing fluid from said passageway into said body vessel;

a conductor disposed in said lead for transmitting electrical signals; and an electrode coupled to said conductor at a distal end portion of said lead, said electrode having a flow passage formed therein.

28. The lead of claim 27, wherein said lead comprises a proximal end portion and a distal end portion, said lead having a lumen extending from said proximal end portion to said distal end portion, said lumen being sized to accept a stylet.

29. The lead of claim 27, wherein lead comprises a proximal end portion and a distal end portion, and wherein said passageway extends from said proximal end portion to said distal end portion and is sized to accept a stylet.

30. The lead of claim 27, wherein said fluid passageway comprises a plurality of inlets and outlets.

31. A lead assembly for implantation in a body vessel, said lead assembly comprising:

a lead having a fluid passageway extending along a given length of said lead, said fluid passageway having an inlet for passing fluid from said body vessel into said passageway and an outlet for passing fluid from said passageway into said body vessel, said lead further having a proximal end portion and a distal end portion and having a lumen being sized to accept a stylet extending from said proximal end portion to said distal end portion;

a conductor being disposed in said lead and extending from said proximal end portion to said distal end portion; and an electrode being coupled to said conductor at said distal end portion of said lead, said electrode having a flow passage formed in said electrode.

32. The lead assembly of claim 31, wherein said flow passage comprises an inlet for passing fluid from said body vessel into said flow passage and an outlet for passing fluid in said flow passage into said body vessel.

33. The lead assembly of claim 31, wherein said flow passage comprises an inlet for passing fluid from said body vessel into said flow passage and an outlet for passing fluid in said flow passage into said inlet of said passageway of said lead.

* * * * *